(12) United States Patent
Liu et al.

(10) Patent No.: US 8,982,346 B2
(45) Date of Patent: Mar. 17, 2015

(54) SYSTEM AND METHOD FOR MEASURING THE ROTATION ANGLE OF OPTICAL ACTIVE SUBSTANCE

(71) Applicant: Industrial Technology Research Institute, Hsin-Chu (TW)

(72) Inventors: Chih-Shang Liu, Hsinchu County (TW); Fu-Cheng Yang, Hsinchu County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 0 days.

(21) Appl. No.: 13/784,947

(22) Filed: Mar. 5, 2013

(65) Prior Publication Data

US 2014/0152988 A1    Jun. 5, 2014

(30) Foreign Application Priority Data

Nov. 30, 2012   (TW) .............. 101145046 A

(51) Int. Cl.
| | |
|---|---|
| *G01J 4/00* | (2006.01) |
| *G01B 9/00* | (2006.01) |
| *A61B 5/145* | (2006.01) |
| *A61B 5/1455* | (2006.01) |
| *G01N 21/21* | (2006.01) |
| *G01J 4/04* | (2006.01) |

(Continued)

(52) U.S. Cl.
CPC .............. *G01B 9/00* (2013.01); *A61B 5/14532* (2013.01); *A61B 5/14558* (2013.01); *G01J 4/04* (2013.01); *G01N 21/21* (2013.01); *A61B 5/6821* (2013.01); *A61B 3/10* (2013.01)
USPC ....................................................... 356/364

(58) Field of Classification Search
USPC ....................................................... 356/364
See application file for complete search history.

(56) References Cited

U.S. PATENT DOCUMENTS

| | | | |
|---|---|---|---|
| 5,009,230 | A | 4/1991 | Hutchinson |
| 5,033,709 | A | 7/1991 | Yuen |

(Continued)

FOREIGN PATENT DOCUMENTS

| | | |
|---|---|---|
| EP | 1387161 A1 | 2/2004 |
| JP | 2002-277387 A | 9/2002 |
| TW | 201239337 A | 10/2012 |

OTHER PUBLICATIONS

Borchert, et al., "A Noninvasive Glucose Monitor: Preliminary Results in Rabbits", 1999, pp. 145-151, vol. 1, Diabetes Technology & Therapeutics.

(Continued)

*Primary Examiner* — Roy M Punnoose
(74) *Attorney, Agent, or Firm* — WPAT, PC; Justin King

(57) ABSTRACT

A system for measuring the rotation angle of optical active substances has a light source, a polarization generation unit; a polarization analyzing unit; a signal generating unit, respectively and electrically coupled to the polarization generation unit and the polarization analyzing unit; a signal processing unit, electrically coupled to the electric signal generating unit; wherein the light source is enabled to emit a beam toward the polarization generation unit for enabling the beam to be polarized into an incident polarized beam while being projected and traveled in an optical path passing through an optical active substance so as to be converted into a emerging beam; and the polarization analyzing unit is positioned to receive and analyze the emerging beam so as to generate a signal to be received and processed by the signal processing unit.

16 Claims, 3 Drawing Sheets

(51) Int. Cl.
*A61B 5/00* (2006.01)
*A61B 3/10* (2006.01)

(56) References Cited

U.S. PATENT DOCUMENTS

| | | | |
|---|---|---|---|
| 5,209,231 A | 5/1993 | Cote et al. | |
| 5,229,834 A * | 7/1993 | Lequime | 356/365 |
| 5,788,632 A * | 8/1998 | Pezzaniti et al. | 600/316 |
| 5,896,198 A | 4/1999 | Chou et al. | |
| 6,181,957 B1 | 1/2001 | Lambert et al. | |
| 6,327,037 B1 * | 12/2001 | Chou et al. | 356/484 |
| 6,704,588 B2 | 3/2004 | Ansari et al. | |
| 6,885,882 B2 | 4/2005 | Cote et al. | |
| 7,038,788 B2 * | 5/2006 | Matsumoto | 356/484 |
| 2010/0234704 A1 * | 9/2010 | Cameron | 600/319 |

OTHER PUBLICATIONS

Lambert, et al., "Glucose determination in human aqueous humor with Raman spectroscopy", May/Jun. 2005, vol. 10(3), Journal of Biomedical Optics.

Wang, et al., "In Vivo, noninvasive glucose monitoring with optical heterodyne polarimetry in a range of 50 mg/dl—100 mg/dl", Jul. 26-27, 2000, vol. 4082, Proceedings of SPIE.

Purvinis, et al, "Noninvasive Polarimetric-Based Glucose Monitoring: An in Vivo Study", Mar. 2011, pp. 380-387, vol. 5, Journal of Diabetes Science and Technology.

Baba, et al, "Effect of temperature, pH, and corneal birefringence on polarimetric glucose monitoring in the eye", Jul. 2002, pp. 321-328, vol. 7, Journal of Biomedical Optics.

Chou, et al, "Noninvasive glucose monitoring in vivo with an optical heterodyne polarimeter", Jun. 1, 1998, pp. 3553-3557, vol. 37, Applied Optics.

Cameron, et al, "Measurement of the Glucose Transport Time Delay Between the Blood and Aqueous Humor of the Eye for the Eventual Development of a Noninvasive Glucose Sensor", 2001, pp. 201-207, vol. 3, Diabetes Technology & Therapeutics.

Chou, et al, "A phase sensitive optical rotation measurement in a scattered chiral medium using a Zeeman laser", 2003, Elsevier B.V.

Ofir Aharon, et al, "Liquid crystal wavelength-independent continuous polarization rotator", Mar. 2010, vol. 49(3), Optical Engineering.

European Patent Office, "Search Report", Dec. 12, 2013.

Taiwan Patent Office, "Office Action", Sep. 2, 2014.

* cited by examiner

SYSTEM AND METHOD FOR MEASURING THE ROTATION ANGLE OF OPTICAL ACTIVE SUBSTANCE

CROSS REFERENCE TO RELATED APPLICATION

This application also claims priority to Taiwan Patent Application No. 101145046 filed in the Taiwan Patent Office on Nov. 30, 2012 the entire content of which is incorporated herein by reference.

TECHNICAL FIELD

The present disclosure relates to a system and method for rotation angle measurement, and more particularly, to a system and method for measuring rotation angle of optical active substances.

BACKGROUND

Although the pathogenesis of diabetes is complicated and still unclarified, it is generally regarded that the modern refine diet is a key factor causing the rapidly increasing worldwide prevalence of diabetes. It is an important task for people with diabetes to measure their glucose level regularly on a daily base.

A glucose meter is a common medical device for determining the approximate concentration of glucose in the blood. There are two types of glucose meters, which are the reflective glucose meter and the transmissive glucose meters. Nevertheless, both types of glucose meters are invasive devices, which require a skin puncture to get a sample of blood for glucose measurement.

It can be a torture mentally and physically for diabetic patients to perform the skin puncture multiple times on a daily base. Therefore, it is in need of a non-invasive glucose meter.

SUMMARY

In an exemplary embodiment, the present disclosure provides a system for measuring rotation angle of optical active substances, which comprises: a light source; a polarization generation unit; a polarization analyzing unit; and a signal generating unit, respectively and electrically coupled to the polarization generation unit and the polarization analyzing unit; wherein the light source is enabled to emit a beam toward the polarization generation unit for enabling the beam to be polarized into an incident polarized beam while being projected and traveled in an optical path passing through an optical active substance so as to be converted into a emerging beam; and the polarization analyzing unit is positioned to receive and analyze the emerging beam so as to generate a signal.

In another exemplary embodiment, the present disclosure provides a method for measuring rotation angle of optical active substances, which comprises the steps of: projecting a beam toward a polarization generating unit for converting the beam into an incident polarized beam; receiving a emerging beam so as to be used as basis for generating a signal; and converting the signal into a rotation angle data.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
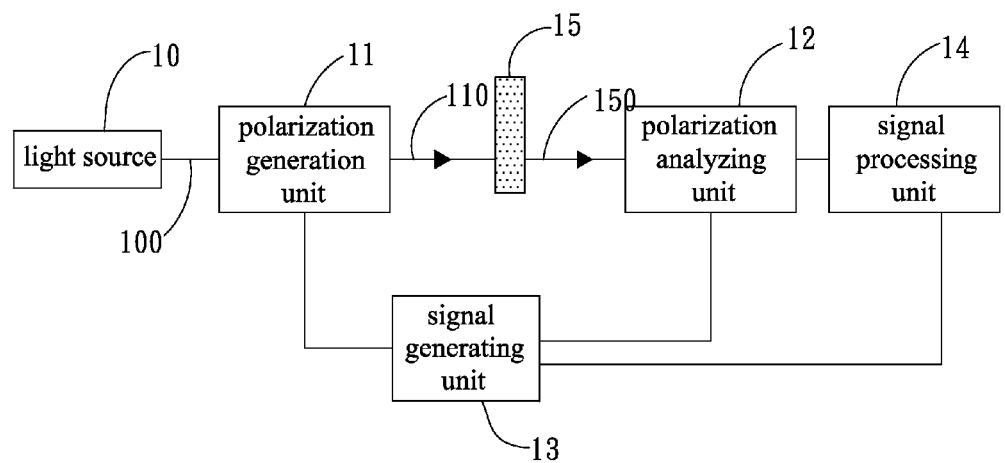
FIG. 1 is a schematic diagram showing a system for measuring rotation angle of optical active substances according to a first embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Please refer to FIG. 1, which is a schematic diagram showing a system for measuring rotation angle of optical active substances according to a first embodiment of the present disclosure. The measurement system shown in the embodiment of FIG. 1 is used for measuring an optical active substance 15, whereas the optical active substance 15 can be any glucose-containing substance, such as aqueous humor, blood, or skin tissue. In this embodiment, the system is used for measuring glucose level of aqueous humor, but is not limited thereby.

As shown in FIG. 1, the system for measuring rotation angle of optical active substances comprises: a light source 10, a polarization generation unit 11, a polarization analyzing unit 12, a signal generating unit 13 and a signal processing unit 14.

The light source 10 is used for emitting a beam 100, whereas the light source in this embodiment can substantially be a light emitting diode, and the beam 100 can be a beam selected from the group consisting of: a continuous wave beam, an amplitude modulation beam, and a frequency modulation beam.

The polarization generating unit 11 is disposed on the optical path of the beam 100, so that the beam 100 can be converting into an incident polarized beam 110 by the polarization generating unit 11.

The optical active substance 15 is disposed on the optical path of the incident polarized beam 110, so that the incident polarized beam 110 can be converting by the optical active substance 15 into a emerging beam 150.

The polarization analyzing unit 12 is disposed on the optical path of the emerging beam 150, by that the polarization analyzing unit 12 is able to generate a signal based upon the emerging beam 150.

The signal generating unit 13 is respectively and electrically connected to the polarization generating unit 11 and the polarization analyzing unit 12, by that the beam 100 of the light source 10 that is projected toward the polarization generation unit 11 is converted into an incident polarized beam 110, and the polarization analyzing unit is enabled to generate a signal according to the emerging beam 150. Moreover, the aforesaid electrical coupling is enabled by a means selected from the group consisting of: a wired connection means and a wireless connection means.

The processing unit 14 is provided for receiving the signal from the polarization analyzing unit 12 so as to generate a rotation angle data accordingly, and then the rotation angle data can be used in a calculation for obtaining a glucose level. In addition, the signal processing unit 14 is electrically connected to the signal generating unit 13 so as to control the signal generating unit 13. In an embodiment, the signal processing unit can be a calculating unit or a cloud unit.

Figure 2:
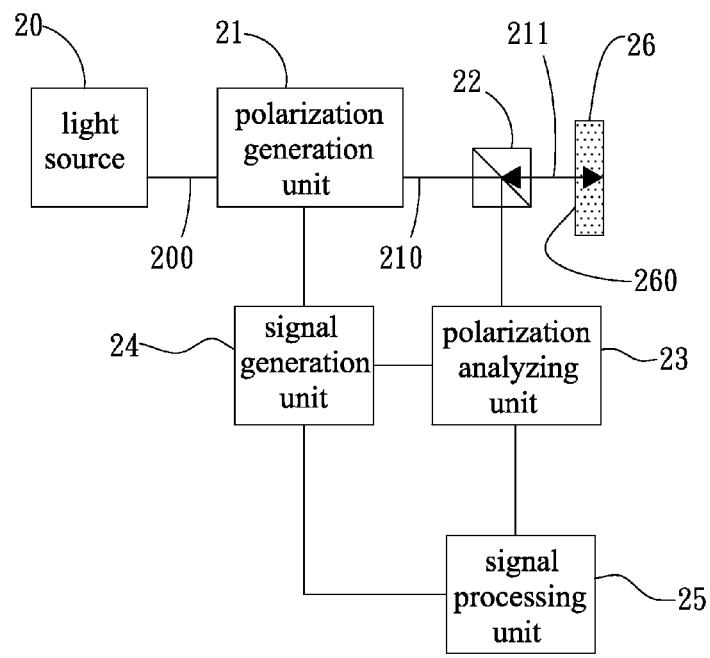
FIG. 2 is a schematic diagram showing a system for measuring rotation angle of optical active substances according to a second embodiment of the present disclosure.

Please refer to FIG. 2, which is a schematic diagram showing a system for measuring rotation angle of optical active substances according to a second embodiment of the present disclosure. Similarly, the system of the present embodiment is used for measuring an optical active substance 26.

In the embodiment of FIG. 2, the measurement system comprises: a light source 20, a polarization generation unit 21, a beam splitting unit 22, a polarization analyzing unit 23, a signal generating unit 24 and a signal processing unit 25.

Operationally, the light source 20 is used for emitting a beam 200; the polarization generating unit 21 is disposed on the optical path of the beam 200, so that the beam 200 can be converting into an incident polarized beam 120 by the polarization generating unit 21; and the beam splitting unit 22 is disposed on the optical path of the incident polarized beam 210 for reflecting the travelling of the incident polarized beam 210 by an angle. It is noted that the beam splitting unit 22 can be a beam splitter.

Moreover, the optical active substance 26 is disposed on the optical path of the incident polarized beam 210 outputted from the beam splitting unit 22. Accordingly, since the beam splitting unit 22 is arranged at a position between the optical active substance 26 and the polarization generation unit 21 whereas the optical active substance 26 is configured with an optical active interface 260, such as the cornea, the incident polarized beam 210 can be reflected by the optical active interface 260 for converting the incident polarized beam 210 into a emerging beam 211 while projecting the emerging beam 211 toward the beam splitting unit 22, and then to the polarization analyzing unit 23 so as to be used as a basis for generating a signal.

The signal generating unit 24 is respectively and electrically connected to the polarization generation unit 21 and the polarization analyzing unit 23; and the signal processing unit 25 is provided for receiving the signal from the polarization analyzing unit, whereas the signal processing unit 25 is electrically connected to the signal generating unit 24.

Figure 3:
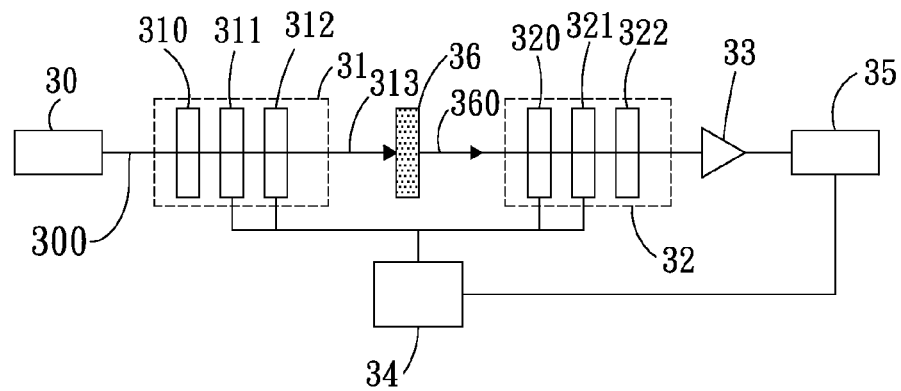
FIG. 3 is a schematic diagram showing a system for measuring rotation angle of optical active substances according to a third embodiment of the present disclosure.

Please refer to FIG. 3, which is a schematic diagram showing a system for measuring rotation angle of optical active substances according to a third embodiment of the present disclosure. Similarly, the system of the present embodiment is used for measuring an optical active substance 36.

In the embodiment of FIG. 3, the measurement system comprises: a light source 30, a polarization generation unit 31, a polarization analyzing unit 32, a light detector 33, a signal generating unit 34 and a signal processing unit 35.

Operationally, the light source 30 is used for emitting a beam 300; the polarization generating unit 31 is disposed on the optical path of the beam 300 and is composed of a polarization element 310, a first phase modulator 311, and a second phase modulator 312. It is noted that the polarization element 310 can be a polarizer or a Nicol prism that is designed to polarize a light into a polarized light; and each of the first and the second phase modulators 311, 312 is substantially a phase modulation device designed for altering the phase of a beam according to a specific pattern.

Thereby, the beam 300 is first being converted into a polarized beam by the polarization element; and then the polarized beam is projected to travel sequentially passing through the first phase modulator 311 and the second phase modulator 312 so as t be converted into an incident polarized beam 313.

Moreover, the optical active substance 36 is disposed on the optical path of the incident polarized beam 313, by that the incident polarized beam 313 is converted into a emerging beam 360. In addition, the polarization analyzing unit 32 is disposed on the optical path of the emerging beam 360 and is composed of a third phase modulator 320, a fourth phase modulator 321 and an analyzer 322. Accordingly, the emerging beam 360 is projected to travel sequentially passing through the third phase modulator 320, the four phase modulator 321 and the analyzer 322. It is noted that the analyzer 322 can be a polarizer provided for determining whether a beam incident thereto is a polarized beam. In this embodiment, the emerging beam 360 is determined by the analyzer 322 to be a polarized beam.

The light detector 33 is disposed on the optical path of the emerging beam 360 after being projected out of the polarization analyzing unit 32, and the light detector 33 is used for generating a signal based upon the emerging beam 360.

The signal generating unit 34 is respectively and electrically connected to the first phase modulator 311, the second phase modulator 312 so as to control the operations of those phase modulators 311, 312, 320, and 321; and the signal processing unit 35, that is electrically connected to the signal generating unit 34, is provided for receiving the signal from the light detector 33 to be used as a base for generating a rotation angle data, whereas the rotation angle data is used in a calculation for obtaining a glucose level.

Figure 4:
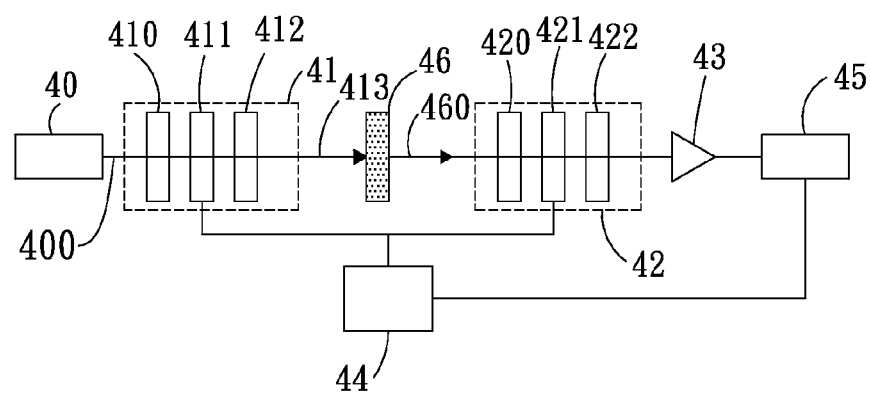
FIG. 4 is a schematic diagram showing a system for measuring rotation angle of optical active substances according to a fourth embodiment of the present disclosure.

Please refer to FIG. 4, which is a schematic diagram showing a system for measuring rotation angle of optical active substances according to a fourth embodiment of the present disclosure. Similarly, the system of the present embodiment is used for measuring an optical active substance 46.

In the embodiment of FIG. 4, the measurement system comprises: a light source 40, a polarization generation unit 41, a polarization analyzing unit 42, a light detector 43, a signal generating unit 44 and a signal processing unit 45.

Operationally, the light source 40 is used for emitting a beam 400; the polarization generating unit 41 is disposed on the optical path of the beam 400 and is composed of a polarization element 410, a phase modulator 411, and a wave plate 412. It is noted that the polarization element 410 is designed to polarize a light into a polarized light; and the phase modulators 411 is substantially a phase modulation device designed for altering the phase of a beam according to a specific pattern. In this embodiment, the phase modulation device is a device selected from the group consisting of: a liquid crystal retardation modulator, a photoelastic modulator, and a Babinet-Soleil compensator. In addition, the wave plate 412 is used for causing a phase difference to a beam travelling passing therethrough, and in this embodiment, the wave plate 412 is substantially a quarter-wave plate.

As shown in FIG. 4, the beam 400 is projected passing sequentially through the polarization element 410, the phase modulator 411 and the wave plate 412 so as to be converted into an incident polarized beam 413.

In a condition when the phase modulator 411 is configured with an axle, the polarization element 410 should be arranged for allowing an included angle ranged between 45 degrees and −45 degrees to be formed between the axle of the polarization element 410 and the axle of the phase modulator 411.

In a condition when the wave plate 412 is configured with an axle, the phase modulator 411 should be arranged for allowing an included angle ranged between 45 degrees and −45 degrees to be formed between the axle of the phase modulator 411 and the axle of the wave plate 412.

Moreover, the optical active substance 46 is disposed on the optical path of the incident polarized beam 413, by that the incident polarized beam 413 is converted into a emerging beam 460.

In addition, the polarization analyzing unit 42 is disposed on the optical path of the emerging beam 460 and is composed of a wave plate 420, a phase modulator 421 and an analyzer 422. In this embodiment, the wave plate 420 is a quarter-wave plate, and the analyzer 422 is a polarizer. Accordingly, the emerging beam 460 is projected to travel sequentially passing through the wave plate 420, the phase modulator 421 and the analyzer 422.

The light detector 43 is disposed on the optical path of the emerging beam 460 after being projected out of the polarization analyzing unit 42, and the light detector 43 is used for generating a signal based upon the emerging beam 460.

The signal generating unit 44 is respectively and electrically connected to the phase modulators 411, 412 so as to control the operations of those phase modulators 411, 412; and the signal processing unit 45, that is electrically connected to the signal generating unit 44, is provided for receiving the signal from the light detector 43 to be used as a base for generating a rotation angle data.

Figure 5:
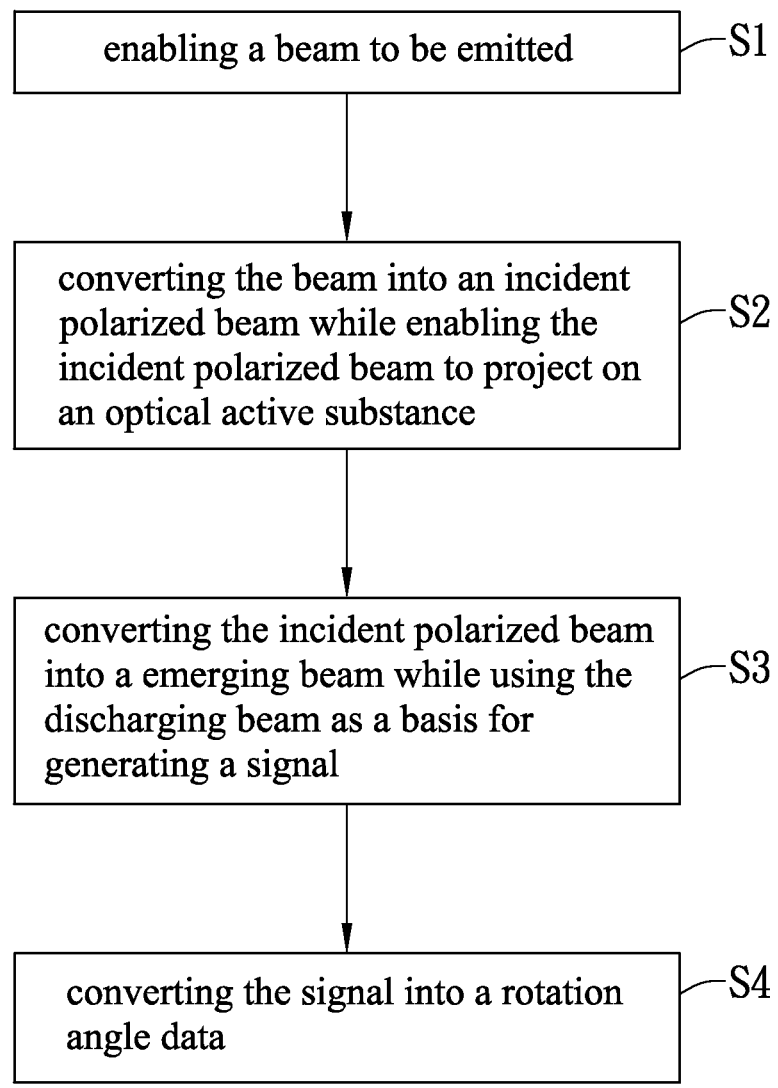
FIG. 5 is a flow chart depicting the steps performed in a method for measuring rotation angle of optical active substances according to an embodiment of the present disclosure.

Please refer to FIG. 5, which is a flow chart depicting the steps performed in a method for measuring rotation angle of optical active substances according to an embodiment of the present disclosure. As shown in FIG. 5, the measurement method comprises the following steps:

S1: enabling a light source to emit a beam, whereas the beam is elected from the group consisting of: a continuous wave beam, an amplitude modulation beam, and a frequency modulation beam, and is characterized by a wavelength ranged between 600 nm and 1700 nm;

S2: converting the beam into an incident polarized beam using components described in the measurement systems of the aforesaid first, second, third and fourth embodiments, in that the beam is polarized by a polarization generation unit into an incident polarized beam while allowing the incident polarized beam to be projected toward an optical active substance, such as an eyeball, a finger, an ear, an so on, and as the incident polarized beam is featured by a specific wavelength, it is free from interference of substances other than the target optical active substance;

S3: enabling the optical active substance to convert the incident polarized beam into a emerging beam, and then by the use of components described in the aforesaid first and second embodiments, the emerging beam is received by the polarization analyzing unit so as to be used as a base for generating a signal; or by the use of components described in the aforesaid third and fourth embodiments, the emerging beam is projected passing sequentially through the polarization analyzing unit and the light detector so as to be used for generating a signal;

S4: enabling a signal processing unit to receive the signal to be applied in a Stokes parameter analysis or a normalization analysis for generating a rotation angle data. In an embodiment when the optical active substance is an eyeball, the rotation angle data can be used in a calculation for obtaining blood glucose level.

In the proceeding of the step S3 and using the measurement system described in the fourth embodiment of FIG. 4 for illustration, the rotation angle data can be represented by the following formula:

$$S=[r_1(t),r_2(t)]=|A*M_2[r_2(t)]*Q_2*R*Q_1*M_1[r_1(t)]*P|^2$$

wherein,
$M_1$ is the phase modulator 411;
$r_1(t)$ is the phase of the phase modulator 411;
$M_2$ is the phase modulator 421;
$r_2(t)$ is the phase of the phase modulator 411;
$[r_1(t), r_2(t)]$ represents a phase-time function;
R is the optical active substance 46;
$Q_1$ is the wave plate 412;
$Q_2$ is another wave plate 42; and
A represent the electric field of the polarization element 422.

For instance, when the axle of the polarization element 410 is orientated at 0 degree, the axle of the phase modulator 411 will be orientated at 45 degrees, the axles of the wave plates 410 and 412 will be orientated at 90 degrees, and the axle of the phase modulator 421 will be orientated at 90 degrees.

If the signal generated from the light detector 42 is a signal of light intensity, the light intensity can be represented as $I[r_1(t),r_2(t)]$. Thus, the rotation angle data can be represented as $$\frac{I[r_1(t_2), r_2(t_2)]}{I[r_1(t_1), r_2(t_1)]} = \frac{S[r_1(t_2), r_2(t_2)]}{S[r_1(t_1), r_2(t_1)]}$$

In the aforesaid formula, the numerators on the left are corresponding to the numerators on the right, while the nominators numerators on the right are corresponding to a theoretical function at time $t_2$; and the denominators on the left are corresponding to the denominators on the right, while the denominators on the right are corresponding to a theoretical function at time $t_1$. Thus, it can be used in a calculation of rotation angle data.

When a Stokes parameter analysis is applied in a calculation of rotation angle data, it is performed using the following formulas:

$$\frac{I[r_1(t), 0°] - I[r_1(t), 180°]}{I[r_1(t), 0°] + I[r_1(t), 180°]} = \frac{S[r_1(t), 0°] - S[r_1(t), 180°]}{S[r_1(t), 0°] + S[r_1(t), 180°]}; \text{ and} \quad \text{Formula 1}$$

$$\frac{I[r_1(t), 90°] - I[r_1(t), 270°]}{I[r_1(t), 90°] + I[r_1(t), 270°]} = \frac{S[r_1(t), 90°] - S[r_1(t), 270°]}{S[r_1(t), 90°] + S[r_1(t), 270°]}. \quad \text{Formula 2}$$

The $S[r_1(t),0°]+S[r_1(t),180°]$ of formula 1 and the $S[r_1(t), 90°]+S[r_1(t),270°]$ of formula 2 can be treated as representative stroke parameter $S_0$, whereas the stroke parameter of formula 1 is referred as $S_1$ and the stroke parameter of formula 2 is referred as $S_2$. Thereby, an optimal solution for the calculation of rotation angle data can be obtained by the combination of formula 1 and formula 2.

To sum up, the present disclosure provide a method and a system for projecting a beam of specific wavelength to a polarization generation unit so as to be polarized into an incident polarized beam, and then enabling the incident polarized beam to shine on and travel passing through an optical active substance so as to form a emerging beam. Thereafter, the emerging beam is projected on a polarization analyzing unit to be used as a basis for generating a signal of light intensity while allowing the signal to be analyzed by a means of Stokes parameter analysis or a reflection rate analysis so as to obtain a rotation angle data. Then the rotation angle data is applied in a calculation for obtaining a glucose level. The method and system of the present disclosure measures a rotation angle of an optical active substances, and then applies the rotation angle in a calculation for obtain the glucose level of the optical active substance, and as a consequence, the measurement method and system are non-invasive measurement method and system.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A system for measuring rotation angle of optically active substance, comprising:
    a light source, emitting a beam;
    a polarization generation unit, converting said beam into a polarized beam incident on said optical active substance, comprising:
        a polarization element;
        a first controllable phase modulator; and
        a second controllable phase modulator;
    a polarization analyzing unit, generating a rotation angle according to an emerging beam, comprising:
        a third controllable phase modulator;
        a fourth controllable phase modulator; and
        an analyzer;
    a signal generating unit, respectively and electrically coupled to the polarization generation unit and the polarization analyzing unit to control said first controllable phase modulator, said second controllable phase modulator, said a third controllable phase modulator, and said fourth controllable phase modulator; and
    a beam splitting unit, arranged at a position between the optically active substance and the polarization generation unit.

2. The system of claim 1, wherein the light source is a light emitting diode.

3. The system of claim 1, wherein said beam is a continuous wave beam, an amplitude modulation beam, or a frequency modulation beam.

4. The system of claim 1, wherein said signal generating unit is electrically coupled to said polarization generation unit and said polarization analyzing unit by a wired connection or a wireless connection.

5. The system of claim 1, further comprising:
    a signal processing unit, electrically connected to said signal generating unit for receiving and processing said signal.

6. The system of claim 1, wherein the beam splitting unit is a beam splitter.

7. The system of claim 1, further comprising:
    a light detector, disposed at a position on an optical path of said emerging beam after said polarization analyzing unit.

8. The system of claim 1, wherein said signal generating unit is respectively and electrically connected to said first controllable phase modulator, said second controllable phase modulator, said third controllable phase modulator and said fourth controllable phase modulator.

9. The system of claim 1, wherein said polarization element is a polarizer or a Nicol prism, said analyzer is a polarizer, and each of said first controllable phase modulator, said second controllable phase modulator, said third controllable phase modulator and said fourth controllable phase modulator is a phase modulation device.

10. The system of claim 9, wherein each of said first controllable phase modulator, said second controllable phase modulator, said third controllable phase modulator and said fourth controllable phase modulator is a device selected from a group consisting of: a liquid crystal retardation modulator, a photoelastic modulator, and a Babinet-Soleil compensator.

11. The system of claim 1, wherein said signal generating unit is respectively and electrically connected to said first controllable phase modulator, said second controllable phase modulator, said third controllable phase modulator and said fourth controllable phase modulator.

12. A method for measuring the rotation angle of an optical active substance, comprising the steps of:
    providing a polarization generation unit, comprising:
        a polarization element;
        a first controllable phase modulator; and
        a second controllable phase modulator;
    projecting a beam toward said polarization generating unit for converting the beam into an incident polarized beam;
    projecting said incident polarized beam into said optical active substance;
    providing a polarization analyzing unit, comprising:
        a third controllable phase modulator;
        a fourth controllable phase modulator; and
        an analyzer;
    receiving an emerging beam from said optical active substance with said polarization analyzing unit;
    generating a signal according to said emerging beam; and
    converting said signal into said rotation angle.

13. The method of claim 12, wherein said beam has a wavelength between 600 nm and 1700 nm.

14. The method of claim 12, wherein said beam is a continuous wave beam, an amplitude modulation beam, or a frequency modulation beam.

15. The method of claim 12, wherein said converting said signal into said rotation angle step is performed by a signal processing unit.

16. The method of claim 15, wherein said signal processing unit employs a Stokes parameter analysis or a normalization analysis for generating said rotation angle.

* * * * *